US012121698B2

(12) United States Patent
Vogelbaum (10) Patent No.: US 12,121,698 B2
(45) Date of Patent: Oct. 22, 2024

(54) MODULAR INFUSION DEVICE AND METHOD OF USE

(71) Applicant: H. Lee Moffitt Cancer Center and Research Institute, Inc., Tampa, FL (US)

(72) Inventor: Michael A. Vogelbaum, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 548 days.

(21) Appl. No.: 17/511,770

(22) Filed: Oct. 27, 2021

(65) Prior Publication Data

US 2022/0047805 A1      Feb. 17, 2022

Related U.S. Application Data

(63) Continuation of application No. PCT/US2020/032585, filed on May 13, 2020.

(60) Provisional application No. 62/874,243, filed on Jul. 15, 2019, provisional application No. 62/847,603, filed on May 14, 2019.

(51) Int. Cl.
*A61M 5/142*      (2006.01)
*A61M 5/168*      (2006.01)

(52) U.S. Cl.
CPC .... *A61M 5/14276* (2013.01); *A61M 5/16804* (2013.01); *A61M 2205/3334* (2013.01)

(58) Field of Classification Search
None
See application file for complete search history.

(56) References Cited

U.S. PATENT DOCUMENTS 8,808,234 B2   8/2014   Vogelbaum et al.
8,979,822 B2   3/2015   Vogelbaum et al.
9,968,765 B2   5/2018   Vogelbaum et al.

FOREIGN PATENT DOCUMENTS

WO      2008020967 A2      2/2008

OTHER PUBLICATIONS

International Preliminary Report on Patentability, for PCT/US2020/032585 filed on May 13, 2020.
International Search Report, for PCT/US2020/032585 filed on May 13, 2020.

*Primary Examiner* — Manuel A Mendez
(74) *Attorney, Agent, or Firm* — Nicholas Pfeifer; Smith & Hopen, P. A.

(57) ABSTRACT

A medical device and method to deliver a liquid solution to a patient's tissue. In particular a medical device that is an infusion device comprising a plurality of delivery tubes with varying lengths and internal diameters so that when the selected plurality of delivery tubes are implanted there is equal impedance to flow through each of the attached delivery tubes resulting in equal flow out of the delivery tubes to regions of interest in the patient's tissue. The plurality of delivery tubes may be attached to an infusion hub in a regular symmetrical pattern or an irregular asymmetrical pattern as required to deliver liquid solution to a plurality of regions of interest in the patient's tissue.

20 Claims, 9 Drawing Sheets

MODULAR INFUSION DEVICE AND METHOD OF USE

CROSS-REFERENCE TO RELATED APPLICATIONS

This nonprovisional application is a continuation of PCT application No. PCT/US20/32585 entitled "MODULAR INFUSION DEVICE AND METHOD OF USE," filed May 13, 2020 by the same inventor, which claims priority to provisional application No. 62/874,243, entitled "MODULAR INFUSION DEVICE AND METHOD OF USE," filed Jul. 15, 2019, and also claims priority to provisional application No. 62/847,603, entitled "SNOWFLAKE INFUSION DEVICE AND METHOD OF USE," filed May 14, 2019 by the same inventor.

TECHNICAL FIELD

Embodiments of this disclosure generally relate to a modular infusion device and method of use. More specifically, embodiments of the disclosure relate to a modular infusion device and method of use that matches impedance of a plurality of delivery tubes to improve uniform infusion of a fluidic drug into a patient's tissue.

BACKGROUND

Varied medical conditions, including treatment of solid tumors, require chronic administration of a pharmaceutically active agent. For example, following surgical excision of a solid tumor, it is advantageous to provide a pharmaceutical fluid via a localized catheter to treat residual neoplastic cells. Providing localized drugs to the tissue can often limit the extent of debulking of the solid tumor from the diseased tissue, which in turn can help to preserve organ function. This can be critical when the neoplastic tissue is e.g., in the brain.

There are several existing systems and methods for providing interstitial treatment after a surgical excision. One method includes inserting wafers infused with a pharmaceutically active agent into the surgically created cavity. These wafers release the drug into the immediate vicinity of the cavity. This method, however, lacks the ability to localize the release of the drug.

There are other systems and methods for providing localized drug delivery, such as convection enhanced delivery of pharmaceutically active agents. Such systems provide drugs under sustained pressure, so the drugs infuse into the tissue. These systems typically involve the use of a plurality of catheters that are individually implanted directly into the tissue surrounding a cavity created by surgical excision of a solid tumor. The catheters are usually inserted from multiple points of origin outside the cavity and a pump forces the drug through the catheters into the tissue in which the catheter is inserted. The open ends of the catheters are precisely positioned to ensure that the drug is delivered to the target tissue rather than the surrounding healthy tissue.

The region of the interest or target tissue, however, can be extensive and irregularly shaped. Current systems and methods, such as those described in International Patent Publication No. WO 2008/020967 to Matsuura et al., account for extensive and irregularly shaped regions of interest. The Matsuura system, however, requires complicated and difficult to manufacture designs and components in order to provide localized drug delivery to extensive and irregularly shaped regions of interest without backflow of the drug, unequal delivery of drug, and leakage of drug.

Accordingly, what is needed is a device and method that both improves the ease of delivering a drug equally to an irregular region of interest and reduces backflow and leakage.

While certain aspects of conventional technologies have been discussed to facilitate disclosure of the instant application, Applicant in no way disclaims these technical aspects, and it is contemplated that the instant application may encompass one or more of the conventional technical aspects discussed herein.

The present disclosure may address one or more of the problems and deficiencies in the art discussed above. However, it is contemplated that this disclosure may prove useful in addressing other problems and deficiencies in many technical areas. Therefore, the present application should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a device and method that both improves the ease of delivering a drug equally to an irregular region of interest and reduces backflow and leakage is now met by a new, useful, and nonobvious invention.

An embodiment of the invention includes an infusion device configured to deliver a fluidic drug to a patient's tissue via a plurality of delivery tubes that have different lengths and internal diameters, but the same flow impedance and flow rate. The infusion device includes a fluid input line fluidically coupled to an infusion hub at an inlet port. Some embodiments include a single input line to reduce complexity and the size of the insertion hole in a patient's tissue. The infusion hub also has a plurality of outlet ports to which the delivery tubes may be secured to bring the delivery tubes in fluidic communication with the infusion hub.

Each of the delivery tubes has an internal lumen, an inlet aperture leading to the internal lumen, and an exit aperture through which the fluidic drug can exit the internal lumen of the delivery tube. The internal lumen of each delivery tube also has a predetermined length to bring the exit aperture into close proximity with a target tissue for delivering the fluidic drug to the target tissue. In addition, each delivery tube is comprised of a predetermined material and thus the internal lumen has a predetermined radial elasticity. Based on the length, internal cross-sectional area, and elasticity of the lumen wall, each delivery tube has a predetermined flow impedance and flow rate. In some embodiments, each delivery tube has the same predetermined impedance and the same flow rate regardless of differences in the properties listed above. In some embodiments, a radius of the internal lumen of the delivery tube is calculated based on $$r = \sqrt[4]{\frac{8\mu L Q}{\Delta P \pi}},$$

where r is the radius of the internal lumen, Q is the flow rate of the fluidic drug, μ is a viscosity of the fluidic drug, L is the length of the internal lumen, and ΔP is the change in pressure of the fluid between the inlet and outlet of the delivery tube, and π is the mathematical constant pi.

Some embodiments include a first indwelling delivery tube attachable to the infusion hub and a second indwelling delivery tube attachable to the infusion hub. The first indwelling delivery tube has an internal lumen, an inlet aperture leading to the internal lumen, and an exit aperture through which the fluidic drug can exit the internal lumen of the delivery tube. The internal lumen is comprised of a predetermined material with a known elasticity. The first indwelling tube further includes a length to bring the exit aperture into close proximity with a target tissue for delivering the fluidic drug to the target tissue.

Likewise, the second indwelling delivery tube has an internal lumen, an inlet aperture leading to the internal lumen, and an exit aperture through which the fluidic drug can exit the internal lumen of the delivery tube. The internal lumen is comprised of a predetermined material with a known elasticity. The second indwelling tube also includes a length to bring the exit aperture into close proximity with a target tissue for delivering the fluidic drug to the target tissue.

The first and second indwelling delivery tubes have at least a different length or a different lumen wall elasticity, but first and second indwelling delivery tubes have a same predetermined flow rate and a same impedance. The flow rate and impedance for each of the first and second indwelling delivery tubes are based on the lengths, cross-sectional areas of the internal lumens, and the known elasticity of the internal lumens.

Some embodiments of the infusion device include a delivery tube connector between the infusion hub and the delivery tubes. The delivery tube connector is adapted to pivot about at least one axis to allow for variability in the placement of the various delivery tubes. In an embodiment, the delivery tube connector is adapted to pivot about multiple axes, include two that are perpendicular to each other. The ability to pivot allows for easy variability in the placement of the various delivery tubes.

An embodiment of the infusion device includes channels extending between the inlet port and the outlet ports in the infusion hub. In an embodiment, the channels each have the same cross-sectional area to ensure an equal delivery of the fluidic drug to each outlet port. In some embodiments, the infusion device further includes a pressurizer fluidically coupled to the infusion device.

Some embodiments include delivery tips fluidically attached to or integrated with the delivery tubes. The delivery tips pierce the target tissue when implanted in a desired location relative to the target tissue. Some embodiments include a plug configured to create a fluid tight seal in outlet ports not connected to delivery tubes.

Some embodiments of the infusion device include different sets of delivery tubes with each set having a distinct predefined flow rate and impedance in comparison to the other sets of delivery tubes. Based on a determination that certain target tissue in the treatment field require different flow rates of the fluidic drug than other target tissue in the treatment field, the system can be tuned to include delivery tubes with different flow rates to deliver more or less fluidic drugs to different target tissues within the treatment field. In other words, an embodiment of the system can be customized with various delivery tubes having different flow rates to enable a single input line and a single hub to provide fluidic drugs to different target tissue at different flow rates. In addition, prior imaging of the treatment field allows a medical professional to customize the system to have the proper length delivery tubes with the desired flow rate to each target tissue.

An embodiment of the present invention includes a method of delivering a fluidic drug to a patient's tissue via multiple delivery tubes of different lengths with each delivery tube having the same flow impedance and flow rate. The method includes retrieving medical imaging of a treatment field within a patient; identifying target tissue to be treated with the fluidic drug; and identifying an intended implantation location for an infusion hub. The infusion hub is fluidically coupled to a fluid input line at an inlet port in the infusion hub and the infusion hub has a plurality of outlet ports.

The method further includes determining a desired impedance or a flow rate of the fluidic drug through a plurality of delivery tubes fluidically coupled to the infusion hub via the outlet ports; determining a length of each delivery tube to bring an exit aperture of the delivery tube into close proximity with the target tissue for delivering the fluidic drug to the target tissue; determining a material composition of each delivery tube to determine an elasticity of the lumen wall of each delivery tube; calculating a cross-sectional area of an internal lumen of each delivery tube based on the desired impedance or flow rate of the fluidic drug through the plurality of delivery tubes, the lumen elasticity, and the length of each delivery tube, such that each delivery tube has the same desired impedance and the same desired flow rate regardless of the length of the delivery tube; and implanting the infusion hub and the delivery tubes into the treatment field, thereby allowing the fluidic drug to be delivered to the patient's target tissue.

Some embodiments of the infusion device include a delivery tube connector between the outlet ports in the infusion hub and the delivery tubes. The delivery tube connectors are adapted to pivot about at least one axis. to allow for variability in the placement of the various delivery tubes. In an embodiment, the delivery tube connectors are adapted to pivot about multiple axes, include two that are perpendicular to each other. The ability to pivot allows for easy variability in the placement of the various delivery tubes.

Some embodiments include different sets of delivery tubes with each set having a distinct predefined flow rate and impedance in comparison to the other sets of delivery tubes. An embodiment of the method includes identifying certain target tissue in the treatment field requiring different flow rates of the fluidic drug than other target tissue in the treatment field. Based on this determination, the system can be tuned to include delivery tubes with different flow rates to deliver more or less fluidic drugs to different target tissues within the treatment field. In other words, the method includes customizing the system with various delivery tubes having different flow rates to enable a single input line and a single hub to provide fluidic drugs to different target tissue at different flow rates. In addition, the prior imaging of the treatment field allows a medical professional to customize the system to have the proper length delivery tubes with the desired flow rate to each target tissue.

Some embodiments include delivery tips fluidically attached to or integrated with the delivery tubes. The delivery tips pierce the target tissue or tissue proximate to the target tissue during implantation.

An embodiment of the infusion device includes channels extending between the inlet port and the outlet ports in the infusion hub. In an embodiment, the channels each have the same cross-sectional area to ensure an equal delivery of the fluidic drug to each outlet port.

In some embodiments, the method includes connecting the infusion device to a pressurizer. In some embodiments, the method includes connecting the fluid input line to a fluid reservoir.

In some embodiments, the method includes the step of closing, in a fluid tight seal, outlet ports not connected to delivery tubes. Some embodiments include a plug configured to create the fluid tight seal in the outlet ports not connected to delivery tubes.

In some embodiments, the step of calculating the cross-sectional area of the internal lumens of each delivery tube includes calculating a radius of the internal lumen of the delivery tube is calculated based on $$r = \sqrt[4]{\frac{8\mu LQ}{\Delta P \pi}},$$

where r is the radius of the internal lumen, Q is the flow rate of the fluidic drug, μ is a viscosity of the fluidic drug, L is the length of the internal lumen, and ΔP is the change in pressure of the fluid between the inlet and outlet of the delivery tube, and π is the mathematical constant pi.

Some embodiments include identifying a subset of delivery tube(s) that should operate in accordance with a second, different predetermined impedance and a second, different predetermined flow rate based on the needs of the patient. Each of delivery tubes in a particular subset has the same predetermined impedance and the same predetermined flow rate regardless of any differences in length, internal cross-sectional area, or lumen wall elasticity. The primary set and subset of delivery tubes are attached to the infusion hub and the resulting system delivers fluidic drugs at a first flow rate and first impedance through the primary set of delivery tubes and at a second flow rate and second impedance through the subset of delivery tubes.

An embodiment of the present invention includes an infusion delivery device kit. The kit includes a fluid input line fluidically coupled or attachable to an infusion hub at an inlet port, a first plurality of delivery tubes, and a second plurality of delivery tubes. The infusion hub has a plurality of outlet ports and the first plurality of delivery tubes and second plurality of delivery tubes are configured to attach to the infusion hub to bring the delivery tubes in fluid communication with the outlet ports on the infusion hub.

Each of the delivery tubes in the first plurality of delivery tubes has the same predetermined first length and the same first internal cross-sectional area. In an embodiment, each of the delivery tubes in the first plurality of delivery tubes are comprised of the same predetermined material and thus have the same lumen wall elasticity. Likewise, each of the delivery tubes in the second plurality of delivery tubes has the same predetermined second length and the same second internal cross-sectional area. The first length is distinct from the second length and the first cross-sectional area is distinct from the second cross-sectional. In an embodiment, each of the delivery tubes in the second plurality of delivery tubes are comprised of the same predetermined material and thus have the same lumen wall elasticity.

In addition, the first plurality of delivery tubes and second plurality of delivery tubes have the same predetermined flow rate and the same impedance. In some embodiments, both the first and second cross-sectional areas are calculated based on $$r = \sqrt[4]{\frac{8\mu LQ}{\Delta P \pi}},$$

where r is the radius of the internal lumen, Q is the flow rate of the fluidic drug, μ is a viscosity of the fluidic drug, L is the length of the internal lumen, and ΔP is the change in pressure of the fluid between the inlet and outlet of the delivery tube, and π is the mathematical constant pi.

In some embodiments, the infusion delivery device kit includes delivery tube connectors between the outlet ports in the infusion hub and the delivery tubes. The delivery tube connectors are adapted to pivot about at least one axis. to allow for variability in the placement of the various delivery tubes. In an embodiment, the delivery tube connectors are adapted to pivot about multiple axes, include two that are perpendicular to each other. The ability to pivot allows for easy variability in the placement of the various delivery tubes.

Some embodiments of the infusion delivery device kit include delivery tips fluidically attached to or integrated with the delivery tubes. The delivery tips pierce the target tissue during implantation.

An embodiment of the infusion delivery device kit includes channels extending between the inlet port and the outlet ports in the infusion hub. In an embodiment, the channels each have the same cross-sectional area to ensure an equal delivery of the fluidic drug to each outlet port.

In some embodiments, infusion delivery device kit further includes a pressurizer configured to be fluidically coupled to the infusion device. Some embodiments include a fluid reservoir configured to be fluidically coupled with the fluid input line.

In some embodiments, infusion delivery device kit includes plugs configured to create a fluid tight seal in the outlet ports or delivery tub connectors not connected to delivery tubes.

In some embodiments, the kit includes a plurality of delivery tubes having different lengths, internal cross-sectional areas, and/or lumen wall elasticities, but each of the delivery tubes has the same impedance and the same flow rate. In some embodiments, the kit includes two or more subsets of delivery tubes, wherein each of delivery tubes in a particular subset has the same predetermined impedance and the same predetermined flow rate regardless of differences in length, internal cross-sectional area, or lumen wall elasticity.

Some embodiments include two or more sets of delivery tubes with each set having a predetermined flow rate and impedance that is distinct from the other sets. With delivery tubes of different flow rates and impedances, the system can be tuned or customized for a particular use. A medical professional will have identified a need to deliver fluidic drugs to certain target tissue in the treatment field at different flow rates in comparison to other target tissue in the treatment field. Based on this determination, the system can be tuned with the delivery tubes having different flow rates to deliver the fluidic drug to various target tissue at different rates. In other words, the system can be customized with various different delivery tubes to enable a single input line and a single hub to provide fluidic drugs to different target tissue at different flow rates. In addition, the prior imaging of the treatment field allows a medical professional to customize the system to have the proper length delivery tubes with the desired flow rate to each target tissue.

Some embodiments include a single kit having two or more sets of delivery tubes with each set having a unique predetermined flow rates and impedances in comparison to the sets. Alternatively, some embodiments include multiple kits with each kit having delivery tubes with the same predetermined flow rates and impedances. The different kits have different flow rates and impedances, but each tube in each kit has the same flow rate and impedance.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

While the specification concludes with claims particularly pointing out and distinctly claiming what are regarded as embodiments of the invention, the advantages of embodiments of the disclosure may be more readily ascertained from the description of certain examples of embodiments of the disclosure when read in conjunction with the accompanying drawings, in which:

DETAILED DESCRIPTION

In the following detailed description, reference is made to the accompanying drawings, which form a part thereof, and within which are shown by way of illustration specific embodiments by which the invention may be practiced. It is to be understood that other embodiments may be used, and structural changes may be made without departing from the scope of the present application. These embodiments are described in sufficient detail to enable those of ordinary skill in the art to practice the present disclosure, and it is to be understood that other embodiments may be utilized, and that structural, logical, and electrical changes may be made within the scope of the disclosure.

From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As used herein, the term "subject," "patient," or "organism" includes humans and animals (e.g., mice, rats, pigs, cats, dogs, and horses).

As used herein, the term "target tissue" refers to the tissue intended to be treated with the catheter device when inserted into a patient. The term "treatment field" as used herein refers to the 3-dimensional area of tissue/space that is intended to be treated with the present invention.

The "fluidic drug" is any fluid substance deemed to be useful in the treatment of a condition of the target tissue. A fluidic drug may include one or more therapeutic substances or agents known to a person of ordinary skill in the art, including but not limited to a drug, a pharmaceutically active agent, a small molecule, an antibody, a protein, a peptide, an oligonucleotide aptamer, an antisense oligonucleotide, and a small interfering RNA (siRNA). The therapeutic substances or agents may be dissolved or suspended as emulsions, micelles, liposomes, or particles in the therapeutic liquid.

An embodiment of the present invention includes a medical device, specifically an infusion device, and method of use, adapted to better deliver a fluidic drug in equal measures to targeted tissue in a patient. An embodiment includes an infusion device and method of use for delivering a fluidic drug to different target tissue using various delivery tubes with each delivery tube having a predetermined flow rate and impedance. In some embodiments, the system is tuned to so that delivery tubes with different flow rates and impedances deliver fluidic drugs to different target tissues at different rates.

Figure 1A:
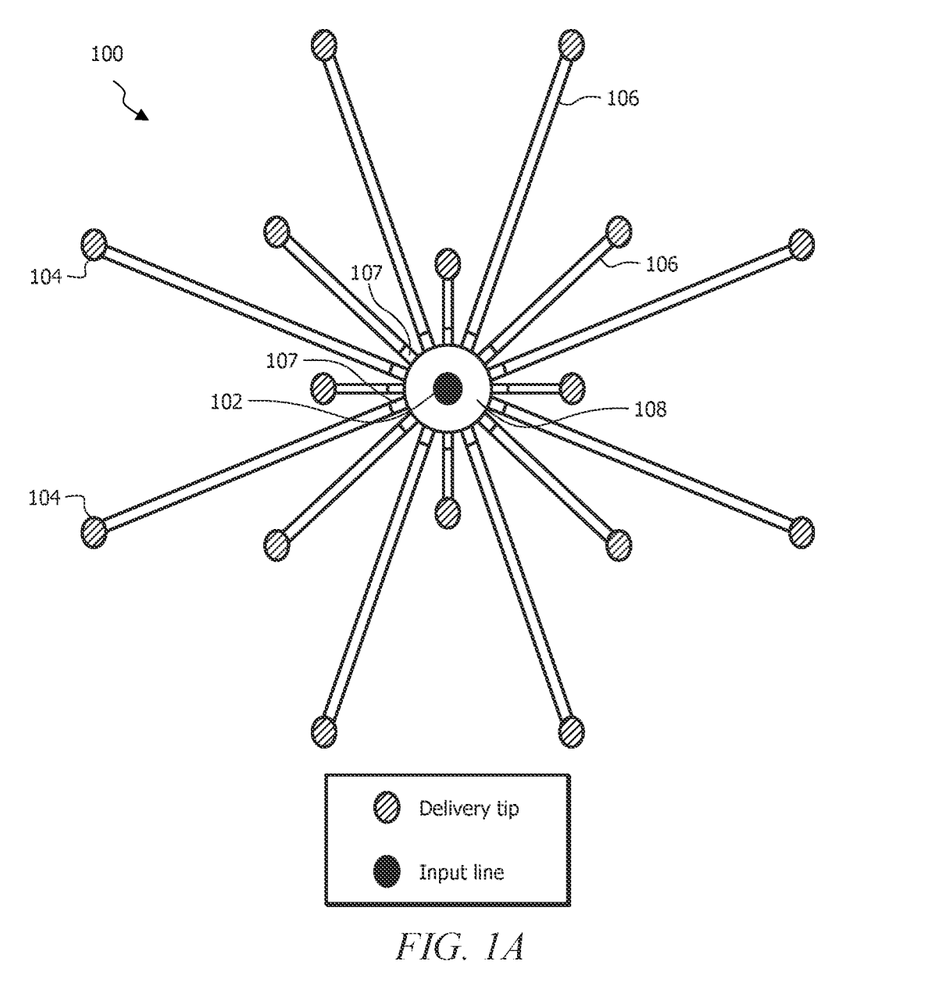
FIG. 1A depicts a top view of a device for drug infusion according to an embodiment of the invention.

Infusion device 100 is biocompatible and can be comprised of any biocompatible elastic material configured to be inserted and implanted into an organism's tissue. As depicted in FIG. 1A, an embodiment of infusion device 100 includes input line 102 attached to input aperture 109 in infusion hub 108 to allow for the flow of drug from input line 102 to infusion hub 108. In addition, delivery tubes 106 extend outwardly from infusion hub 108 to deliver fluidic drugs to targeted tissue. Some embodiments of infusion device 100 include a single input line 102 connected to a single input aperture 109 to reduce the number of lines passing into a patient.

Figure 1B:
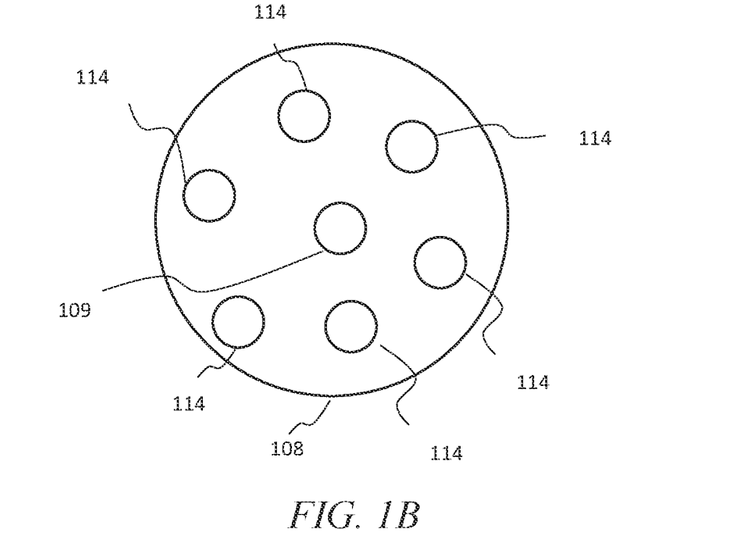
FIG. 1B depicts an embodiment of the infusion hub.
Figure 1C:
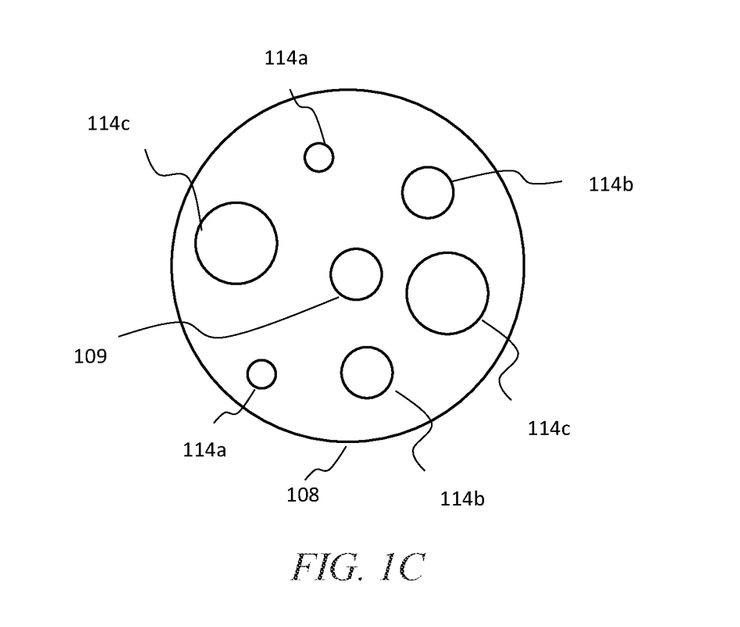
FIG. 1C depicts an embodiment of the infusion hub.

As depicted in FIGS. 1B-1C, infusion hub 108 includes a plurality of ports 114 to which hollow delivery tubes 106 are secured in fluidic communication. As depicted in FIG. 1B, an embodiment includes infusion hub 108 having a plurality of ports 114 of the same general diameter. Alternatively, an embodiment includes at least one variation in the port diameters. For example, FIG. 1C depicts an embodiment having ports 114a-114c with diameters corresponding to delivery tubes with varying outer diameters or varying diameters at their connection ends.

In some embodiments the infusion device 100 also has delivery tube connectors 107 which attach delivery tubes 106 to the infusion hub 108. In some embodiments these delivery tube connectors 107 are configured to attach delivery tubes 106 of various internal diameters to allow for the modular attachment of a plurality of varied delivery tubes 106 to the infusion hub 108. In some embodiments, delivery tube connectors 107 are configured to attach delivery tubes 106 of various external diameters to allow for the modular attachment of a plurality of varied delivery tubes 106 to the infusion hub 108. For example, there may be different delivery tube connectors 107 having different sized distal ends to couple to delivery tubes 106 with different sized proximal ends.

Delivery tubes 106 are attachable to delivery tube connectors 107 or to ports 114 to bring delivery tubes 106 into fluidic communication with hub 108. Delivery tubes 106 may be secured by any connection mechanism designed to prevent leakage of a fluidic solution from the infusion device 100. These connection mechanisms include, but are not limited to, luer locks, internal threads/helical grooves, external threads/helical grooves, a locking nut, a circumferentially raised ridge fitting into a circumferentially depressed section, stopcock connection, tapered fitted end, stepped tubing, barbed tubing, bayonet fittings, compression fittings, flare connectors, funnel connectors, large-bore connectors, giant-bore connectors, or any suitable combination thereof.

Delivery tubes 106 may be linear or curvilinear and may be comprised of a flexible material to adjust the shape of delivery tubes 106. In addition, delivery tubes 106 may be adapted for implantation into solid tissue of a patient. In some embodiments, delivery tubes 106 may be comprise one or multiple thick segments, rings or bulges on the outside of the shaft to reduce backflow around the catheter track and thus promote uptake of the liquid solution into the patient's tissue.

Delivery tubes 106 have internal lumen 105 through which fluidic drugs may flow. Internal lumens 105 have a predetermined lumen wall elasticity based on the material composition of delivery tubes 106. The elasticity of the lumen wall has a direct impact on the flow impedance and thus the flow rate.

Delivery tubes 106 include delivery tip 104, and one or more openings, apertures or ports at or relatively near delivery tip 104, or on any portion of delivery tubes 106 adapted to be in direct contact with the patient's tissue. Delivery tips 104 may have one opening or multiple openings to internal lumen 105.

Figure 1D:
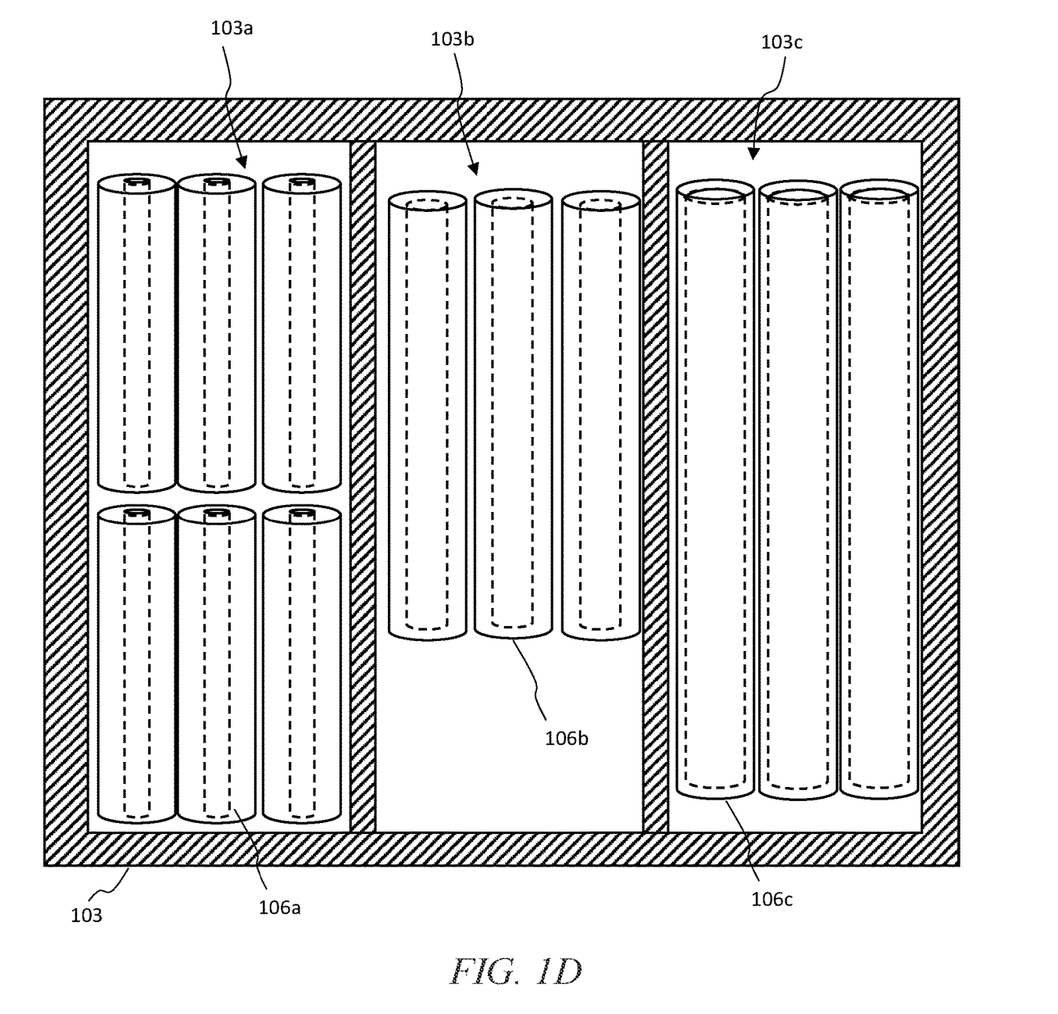
FIG. 1D depicts a delivery tube kit according to an embodiment of the present invention.
Figure 1E:
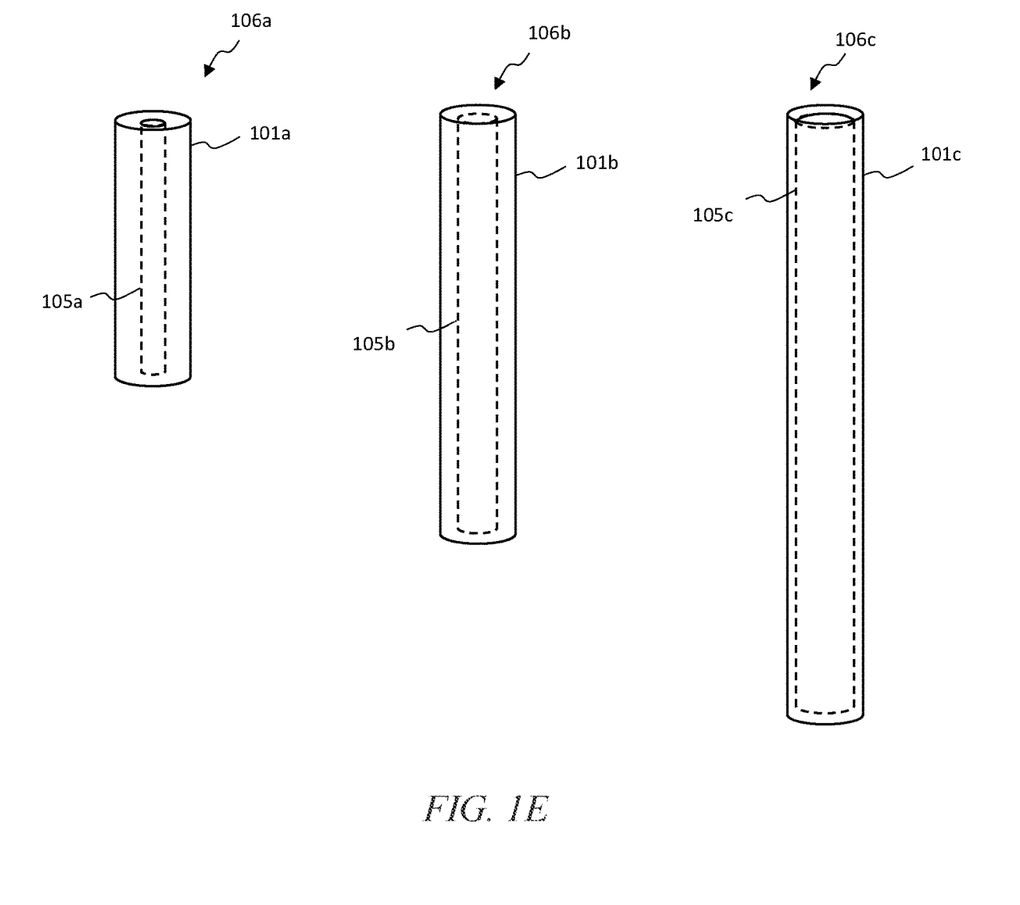
FIG. 1E depicts a comparison of delivery tubes of different dimensions according to an embodiment of the present invention.

As best depicted in FIGS. 1C-1D, some embodiments of infusion device 100 have delivery tubes 106 of different lengths with internal lumens 105 of varying internal diameters. In an embodiment, the diameters or cross-sectional areas of outer surfaces 101a-101c of delivery tubes 106a-106c are consistent to enable each delivery tube 106a-106c to attach to any port 114 or tube connector 107 in hub 108. External surfaces 101 may have any cross-sectional shape including round, ovoid, square, or triangular so long as they can interface with ports 114 or connectors 107 in a leak free manner. Likewise, internal lumens 105a-105c may have any cross-sectional shape including round, ovoid, square, or triangular.

In some embodiments, delivery tubes 106 are provided for an end user, such as a physician or surgeon, in sets that are provided in kit 103 as depicted in FIG. 1D. The exemplary depicted kit 103 includes sub compartments 103a, 103b, and 103c, each respectively housing a plurality of short delivery tubes 106a, medium length delivery tubes 106b, and long delivery tubes 106c. Each lumen 105a, 105b, 105c has a different internal diameter/cross-sectional area based on the length of the lumen. In some embodiments, kit 103 includes a greater diversity of delivery tubes 106 in terms of length. However, each delivery tube has a lumen with a known radial elasticity and a predetermined cross-sectional area that is a function of its length. As a result, all of the delivery tubes in a given kit have the same flow rate and flow impedance.

As depicted best in FIGS. 1C-1D, longer delivery tubes 106 have internal lumens with proportionally larger cross-sectional areas. The relationship between the length and the cross-sectional areas of internal lumens 105a, 105b, 105c is proportional to ensure that each delivery tube 106a-106c provides the same impedance to the flow of liquid through the various delivery tubes. An equal impedance among the plurality of attached delivery tubes 106a-106c ensures that the rate of flow of liquid solution flowing through each delivery tube 106a-106c is consistent. In the absence of this equal impedance more of the liquid solution would flow out of the delivery tube providing the least resistance to the flow of liquid.

In some embodiments, the ratio of cross-sectional area to length of delivery tubes 106 is calculated using equation 1:

$$r = \sqrt[4]{\frac{8\mu LQ}{\Delta P \pi}} \quad \text{Equation 1}$$

where Q is flow rate, $\pi$ is the mathematical constant pi, $\Delta P$ is the pressure differential between the inlet and outlet of the delivery tube, r is the radius of the internal lumen of the delivery tube, $\mu$ is the viscosity of the fluid, and L is the length of the internal lumen between the inlet and outlet of the delivery tube. By setting the pressure differential and flow rate to a constant, the radius or cross-sectional area of the internal lumen of each delivery tube can be calculated based on the intended length of the delivery tube. Vice versa, the length of each delivery tube can be determined using the known radius or cross-sectional area of the internal lumen of each delivery tube. Thus, each tube can be specifically designed to ensure each tube has the same flow rate and pressure, regardless of the differences in lengths, to treat asymmetric treatment fields.

In some embodiments, the kit includes a plurality of delivery tubes having different lengths, internal cross-sectional areas, and/or lumen wall elasticities. However, each of the delivery tubes has the same impedance and the same flow rate. In some embodiments, the kit includes two or more subsets of delivery tubes, wherein each of delivery tubes in a particular subset has the same predetermined impedance and the same predetermined flow rate regardless of differences in length, internal cross-sectional area, or lumen wall elasticity.

Some embodiments include two or more sets of delivery tubes with each set having a predetermined different flow rate and impedance. With delivery tubes of different flow rates and impedances, the system can be tuned or customized for a particular use. A medical professional will have identified a need to deliver fluidic drugs to certain target tissue in the treatment field at different flow rates than other target tissue in the treatment field. Based on this determination, the system can be tuned with the delivery tubes having different flow rates to deliver the fluidic drug to various target tissue at different rates. In other words, the system can be customized with various different delivery tubes to enable a single input line and a single hub to provide fluidic drugs to different target tissue at different flow rates. In addition, prior imaging of the treatment field allows a medical professional to customize the system to have the proper length delivery tubes with the desired flow rate to each target tissue.

Some embodiments include a single kit having two or more sets of delivery tubes with each set having a unique predetermined flow rate and impedance. Alternatively, some embodiments include multiple kits. Each kit has delivery tubes with the same predetermined flow rates and impedances, but the flow rates and impedances vary from kit to kit.

In embodiments having multiple kits, each kit may be coded, such as with color coding, to avoid confusing delivery tubes 106 from different kits. The specific coding ensures that a user know the impedance and flow rate of a particular delivery tube. In some embodiments, the markings indicate the proximal end of the delivery tube 106 which is configured to be attached to infusion hub 108.

In some embodiments, each of the plurality of delivery tubes 106 has markings (not depicted) to indicate the lengths that delivery tubes 106 may be cut down to maintain equal flow out of each of the chosen and customized delivery tubes 106. Some embodiments include choke tubes that can be inserted into the internal lumens 105 to artificially restrict the diameter of internal lumens 105. The choke tubes have a smaller internal diameter to coincide with a reduction in the length of a delivery tube. The choke tubes in conjunction with predetermined cut lines, allow longer delivery tubes 106c or 106b to be easily cut down and converted into a shorter delivery tube with an effective smaller internal cross-sectional area. The choke tubes may have indicators that are similar in style, shape, or color, to the predetermined cut lines. As a result, the indicators on the choke tubes clarify which tubes coincide with which cut lines. In addition, or alternatively, the choke tubes of certain internal diameters may have a predetermined length that matches the tube length after it has been cut at a certain cut line.

Delivery tubes 106 may be attached to infusion hub 108 in any configuration, including regular and symmetrical configurations or irregular asymmetrical configurations. In some embodiments, infusion hub 108 may a plurality of output ports ranging between 2 and 12 ports. In some embodiments, infusion hub 108 has a plurality of ports ranging between one up to two dozen openings/ports to which delivery tubes 106 may be fluidically coupled. In some embodiments, infusion hub 108 may have three dozen openings/ports. In some embodiments, infusion hub 108 may have four dozen openings/ports.

In some embodiments, delivery tubes 106 may be inserted into the organism sequentially, simultaneously, or in subsets of the plurality to accommodate various sized cavities in which the device will be implanted. Likewise, infusion hub 108 may be provided in multiple sizes to accommodate various sized cavities in which the hub will be implanted. The plurality of various sized infusion hubs 108 each include input apertures 109 providing an opening for delivering fluid from input line 102 into the center of infusion hub 108. In some embodiments, the plurality of various sized infusion hubs 108 have a set number of small ports 114a, medium-sized ports 114b, and large ports 114c to which delivery tubes 106 with various internal diameters will attach.

In some embodiments a plurality of infusion hub plugs 113 are provided to close ports 114 in infusion hub 108 that are not in use, i.e., ports 114 to which a delivery tube 106 is not attached. The infusion hub plugs 113 prevent leakage from infusion hub 108, which would impair the system's ability to deliver fluids to each target tissue 112 at a predetermined flow rate or impedance. In some embodiments infusion hub 108 is provided with the infusion hub plugs attached to infusion hub 108 so the end user can remove the infusion hub plug and attach an appropriately sized delivery tube 106. In some embodiments, plugs 113 are configured to plug delivery tube connectors 107 to stop the flow of fluid out of an unused delivery tub connector 107.

Figure 2A:
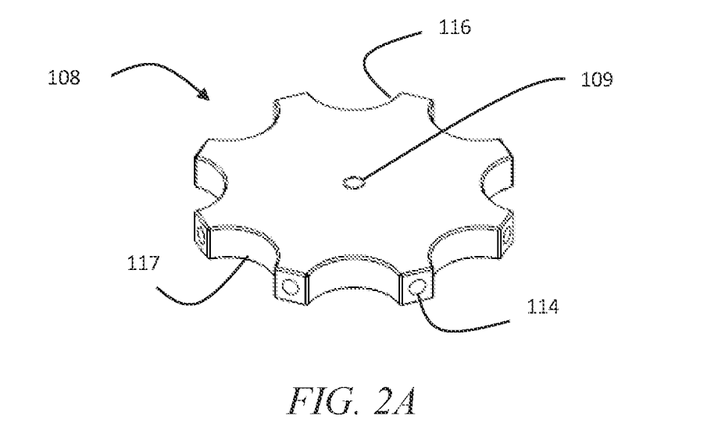
FIG. 2A is a perspective view of an embodiment of the infusion hub.
Figure 2B:
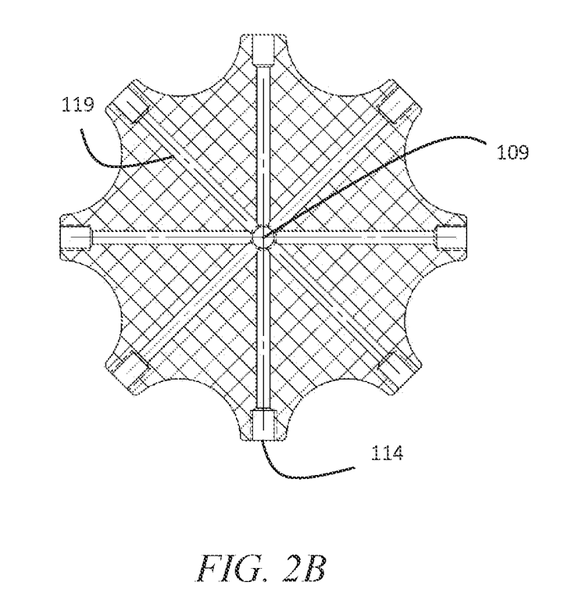
FIG. 2B is a cross-sectional view of an embodiment of the infusion hub.

As depicted in FIGS. 2A-2B, an embodiment of infusion hub 108 includes protruding ridges 116 with intermediate arched supports 117. Intermediate arched supports 117 increase the structural rigidity of infusion hub 108 and provide finger holds for easy handling during an operation.

Ports 114 are located at the distal edge of protruding ridges 116 and are configured to attach to a plurality of delivery tubes 106. Ports 114 are fluidly coupled to inlet aperture 109 through internal channels 119. In an embodiment, each of channels 119 is of the same diameter to ensure equal flow of fluid from inlet aperture 109 to ports 114. In an embodiment, each port 114 is of the same diameter to ensure equal flow rates through inlet aperture 109 to delivery tubes 106.

As shown in FIG. 2B, infusion device 100 further includes input line 102 attached to inlet aperture 109 on infusion hub 108 to allow for the flow of fluid from input line 102 to infusion hub 108 then out to the plurality of delivery tubes 106 and finally out of delivery tips 104. In some embodiments, input line 102 may be configured with attachment mechanism 111 at the proximal end to facilitate attachment of input line 102 to a fluidic input device, another hollow tube, or a plug.

Figure 2C:
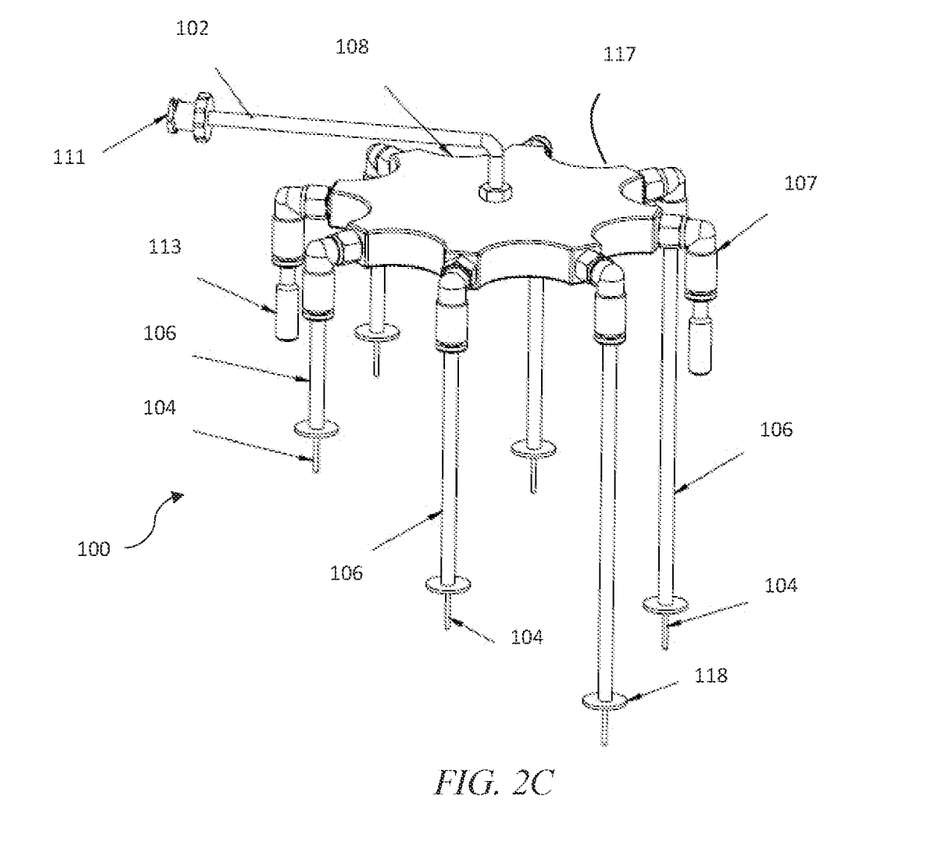
FIG. 2C is a perspective view of an embodiment of the present invention.

As depicted, infusion hub 108 has a plurality of ridges 116 to which elbow-shaped delivery tube connectors 107 are attached. Delivery tube connectors 107 may be attached to infusion hub 108 by any connection mechanism designed to prevent leakage of a fluidic solution from the infusion device 100. These connection mechanisms include, but are not limited to, luer locks, internal threads/helical grooves, external threads/helical grooves, a locking nut, a circumferentially raised ridge fitting into a circumferentially depressed section, stopcock connection, tapered fitted end, stepped tubing, barbed tubing, bayonet fittings, compression fittings, flare connectors, funnel connectors, large-bore connectors, giant-bore connectors, or any suitable combination thereof. Some embodiments of delivery tube connectors 107 may have a hollow shape other than an elbow-shape.

In some embodiments, delivery tube connectors 107 are configured to rotate about an axis, such as the one axially aligned with the center axis of port 114. The ability to rotate about an axis increase the devices ability to reach target tissue in various locations. The rotational component may any rotational, leak-free mechanism known to a person of ordinary skill in the art, such as a fluid-tight swivel joint. In some embodiments, delivery tube connectors 107 have multiple degrees of freedom (i.e., multiple rotational axes) to allow for three-dimensional positioning of delivery tubes 106.

The plurality of delivery tubes 106 are in turn attached to delivery tube connectors 107 so that delivery tip 104 is in fluid communication with infusion hub 108. Delivery tubes 106 may be attached to delivery tube connectors 107 by any connection mechanism designed to prevent leakage of a fluidic solution. These connection mechanisms include, but are not limited to, luer locks, internal threads/helical grooves, external threads/helical grooves, a locking nut, a circumferentially raised ridge fitting into a circumferentially depressed section, stopcock connection, tapered fitted end, stepped tubing, barbed tubing, bayonet fittings, compression fittings, flare connectors, funnel connectors, large-bore connectors, giant-bore connectors, or any suitable combination thereof.

Delivery tubes 106 may further comprise a non-cutting rounded delivery tip 104 to minimize trauma to tissues during implantation. Delivery tips 104 may be equipped with penetration stops 118 intended to minimize tissue trauma as delivery tips 104 pierce the target tissue during insertion/implantation. Stops 118 may be comprised of a hard substance such as metal or a soft polymeric material and are greater in diameter than distal ends 104 to prevent unnecessarily deep penetration into a patient's tissue.

Figure 2D:
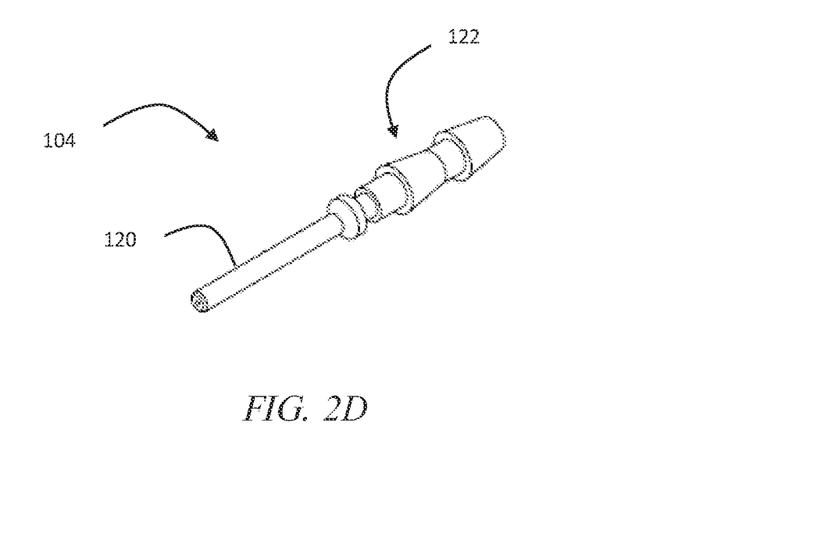
FIG. 2D is a perspective view of an embodiment of the distal tip of a delivery tube.
Figure 2E:
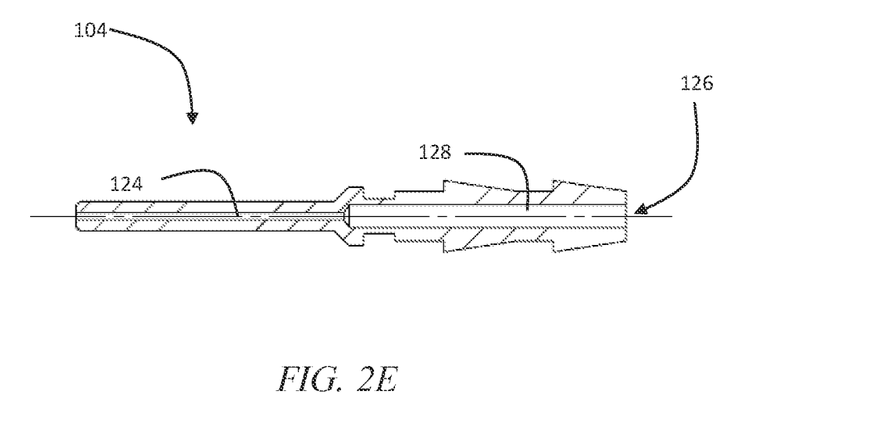
FIG. 2E is a cross-sectional view of an embodiment of the distal tip of a delivery tube.

FIGS. 2D-2E provide greater detail of delivery tip 104. The distal end 120 of the delivery tip 104 is configured to be inserted into a subject's tissue. The proximal end 122 of the delivery tip 104 is configured to attach to one of delivery tubes 106 or delivery tip 104 is integrated with delivery tubes 106. In addition, as depicted in FIG. 2E, distal portion 124 of internal lumen 126 of delivery tip 104 has a cross-sectional area that is smaller than proximal portion 128. This change in cross-sectional area helps prevent backflow of the fluids. In some embodiments delivery tubes 106 are configured for one-way flow with a series of valves disposed within the lumen of delivery tubes 106 to prevent backflow of the liquid solution.

Figure 3A:
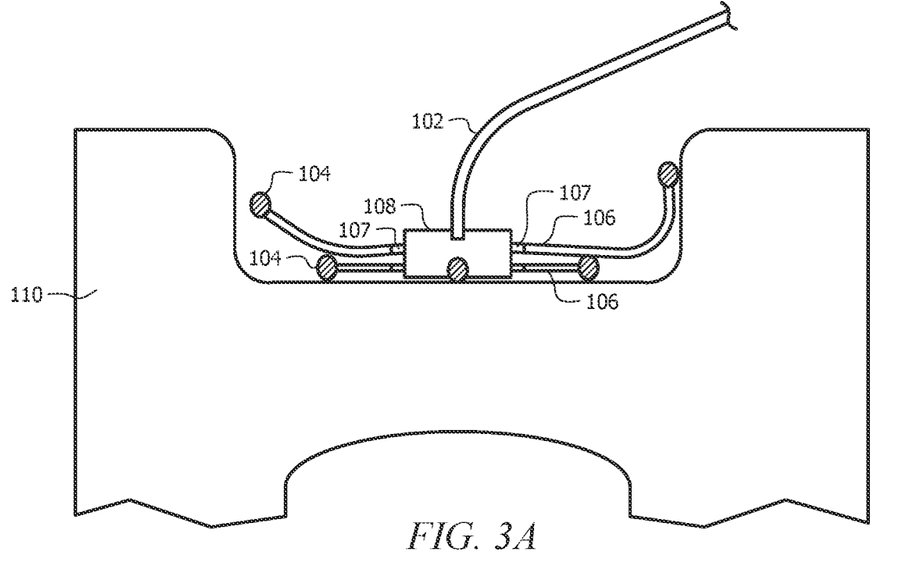
FIG. 3A is a schematic cross-section view of an embodiment of the present invention placed in a treatment field in an organism.

As depicted in FIG. 3A, infusion device 100 can be implanted within a treatment field within patient's tissue 110, as in a cavity left after a surgical excision of diseased tissue. Input line 102 is configured to be both implanted into a patient's tissue 110 and extend out of the patient's skin. Infusion device 100 is attached to a liquid supply system external to the patient's skin via input line 102. Some embodiments include a pressurizer (not depicted) that is adapted to apply pressure to the liquid solution passing through input line 102. The fluidic drug can thus be delivered to target tissue 112 under pressure. Infusion device 100 can be used to administer a liquid solution at a variety of pressures and flow rates. In addition, the liquid solution can be administered continuously, intermittently, at various rates, and for various periods of time.

Figure 3B:
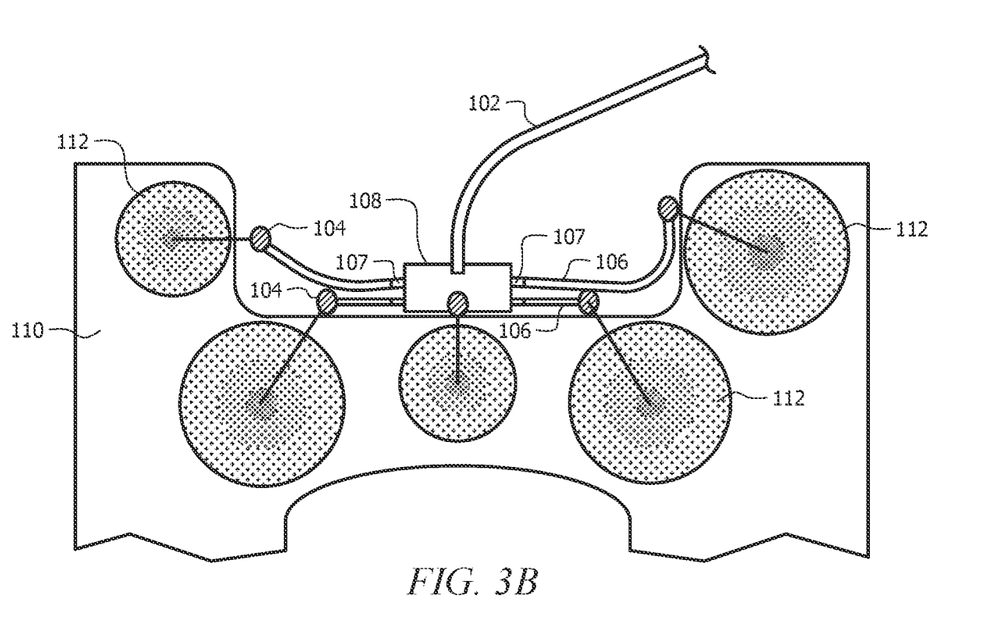
FIG. 3B is a schematic cross-section view of a device for drug infusion placed in a treatment field in an organism according to an embodiment of the invention.

As best depicted in FIG. 3B, infusion device 100 provides fluid to target tissue 112 in patient's tissue 110. Target tissue 112 will vary depending inhomogeneous tissue density, variable interstitial pressure, variable capillary density, or variations related to disease states. Target tissue 112 may be large and irregularly shaped. Based on the locations of target tissue 112, the system can be customized to include a specific number of delivery tubes 106, with each having a predetermined location and length. Regardless of length, all delivery tubes 106 can be designed to deliver fluidic drugs at the same flow rate and impedance. Flow rate and impendence can be predesigned based on the dimensions of the internal lumens (e.g. lengths and cross-sectional areas) and the lumen wall elasticity, which can be based on wall thickness and material/mechanical properties.

In some embodiments, infusion device 100 is configured to be chronically implanted into a patient. The implantation may be for a period of hours, days, week, months, or years, as is required to treat target tissue 112 with different pharmaceutically active agents which may be needed for these periods of time. Delivery tubes 106 may be implanted into patient's tissue 110 to provide for overlapping treatment fields. These treatment fields may be uniform or irregular. Optimal positioning of delivery tubes 106 and infusion hub 108 will ensure the liquid solution is delivered to the entire intended treatment field in target tissue 112 while minimizing exposure of the liquid solution to uninvolved regions of the tissue or organ. The resistance to liquid flow into tissue is often high, so delivery rates are relatively low and the one or plurality of openings at the delivery tip 104 facilitates these low flow rates.

The novel method of the present invention includes designing, implanting, and operating an infusion device configured to deliver fluidic drugs through at least a first set of delivery tubes at a predetermined flow rate and impedance regardless of the individual lengths, cross-sectional areas, or lumen wall elasticities of the various delivery tubes in the first set. Some embodiments include designing a second set of delivery tubes configured to deliver fluidic drugs at a second predetermined flow rate and impedance regardless of the individual lengths, cross-sectional areas, or lumen wall elasticities of the various delivery tubes in the second set. Some embodiments include more than two sets operating under the same principles of common flow rates and impedance amongst delivery tubes within a set.

The method of implantation includes inserting infusion device 100 into a patient so infusion device 100 is implanted under the patient's skin and input line 102 extends out of the patient's skin. Infusion device 100 delivers liquid solution from input line 102 through infusion hub 108, then through attached delivery tubes 106 and out of delivery tips 104 to target tissue 112 in patient's tissue 110. In some embodiments, the rigidity of delivery tubes 106 is augmented by a guide wire (not depicted) which can be removed once the delivery tube 106 is implanted into the patient's tissue 110. The method of implantation ensures that the liquid solution passing through delivery tubes 106 is reliably distributed into target tissue 112 with less risk of underexposing the watershed areas between various target tissue 112.

Figure 4:
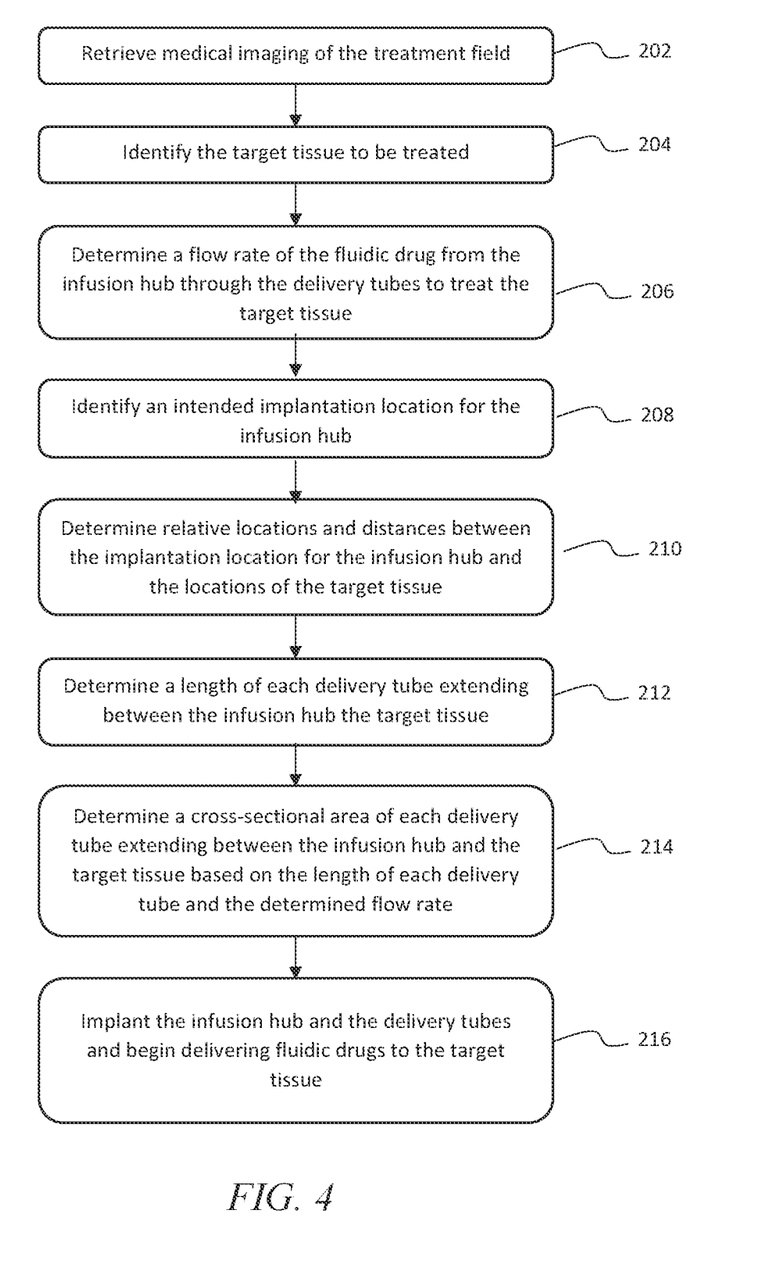
FIG. 4 is flowchart of an embodiment of the novel method of the present invention.

In some embodiments, the method of implanting the infusion device 100 can be used in conjunction with image-based pretreatment planning as exemplified in FIG. 4. The pretreatment planning allows for pre-customization of delivery tubes 106 to implant delivery tips 104 into target tissue 112 with varied and even irregular shapes. The pretreatment planning can provide a 3-dimensional treatment field to map how long and how many delivery tubes 106 are needed to deliver the desired liquid solution to target tissue 112. The 3-dimensional topography of the treatment field and target tissue 112 can be defined before implantation using computerized axial tomography (CT scans), magnetic resonance imaging (MRI), Positron Emission Tomography (PET scans), PET-CT, or other tissue imaging technologies. As conditions change during the implantation of infusion device 100 delivery tubes 106 may be further customized before being attached to infusion hub 108. In some embodiments delivery tubes 106 contain markings that are radiopaque or paramagnetic substances to improve visualization by imaging technologies. Implantation of delivery tubes 106 may be monitored by various imaging technologies to ensure proper placement of delivery tips 104. In some embodiments a radiofrequency emitting probe can be used to determine stereotactic coordinates for emplacement of the objects with the patient's tissue, which can be used in conjunction with a preoperative MRI, or other imaging, to guide the exact implantation of delivery tip 104 within target tissue 112.

In the embodiment depicted in FIG. 4, the novel method includes retrieving medical imaging of the treatment field in step 202 and identifying the target tissue for treatment in step 204. In step 206, the flow rate and/or the flow impedance of the fluidic drug from the infusion hub through the delivery tubes is determined to treat the target tissue. Then, an intended implantation site is identified for the infusion hub in step 208. Once the infusion hub implantation location is determined, the relative locations and distances between the infusion hub and the target tissue are determined in step 210. In step 212, the length of each delivery tube extending between the infusion hub to the target tissue is determined. Based on the length of the delivery tubes and the flow rate or the impedance of the fluidic drug, the cross-sectional area of each tube is calculated in step 214. Finally, in step 216, the infusion hub and the delivery tubes are implanted, and fluidic drugs are delivered to the target tissue.

An embodiment includes a step of determining an elasticity of the lumen wall which impacts the impedance and flow rate of the fluid through the lumen. In an embodiment of the novel method includes identifying the material of the delivery tubes to determine the elasticity of the lumen wall.

In some embodiments, the step of calculating the cross-sectional area of the internal lumens of each delivery tube includes calculating a radius of the internal lumen of the delivery tube is calculated based on $$r = \sqrt[4]{\frac{8\mu LQ}{\Delta P \pi}},$$

where r is the radius of the internal lumen, Q is the flow rate of the fluidic drug, μ is a viscosity of the fluidic drug, L is the length of the internal lumen, and ΔP is the change in pressure of the fluid between the inlet and outlet of the delivery tube, and π is the mathematical constant pi.

Some embodiments include identifying a need for a subset of delivery tube(s) that operate in accordance with a second, different predetermined impedance and a second, different predetermined flow rate based on the needs of the patient. This need can be based on a determination that certain target tissue in the treatment field require different flow rates of the fluidic drug than other target tissue in the treatment field. Based on this determination, the system can be tuned to include delivery tubes with different flow rates to deliver more or less fluidic drugs to different target tissues within the treatment field. In other words, the system can be customized with various delivery tubes having different flow rates to enable a single input line and a single hub to provide fluidic drugs to different target tissue at different flow rates. In addition, prior imaging of the treatment field allows a medical professional to customize the system to have the proper length delivery tubes with the desired flow rate to each target tissue.

Each of delivery tubes in a particular set/subset has the same predetermined impedance and the same predetermined flow rate regardless of any differences in length, internal cross-sectional area, or lumen wall elasticity. The predetermined flow rates and impedances can vary amongst the sets/subsets. The primary set and subset(s) of delivery tubes can be attached to the infusion hub and the resulting system delivers fluidic drugs at a first flow rate and first impedance through the primary set of delivery tubes and at a second flow rate and second impedance through the subset of delivery tubes. If there are multiple subsets, then the fluidic drugs are delivered at different flow rates and impedances based on the number of different sets.

The advantages set forth above, and those made apparent from the foregoing description, are efficiently attained. While the disclosure is susceptible to various modifications and implementation in alternative forms, specific embodiments have been shown by way of non-limiting example in the drawings and have been described in detail herein. Since certain changes may be made in the above construction without departing from the scope of the instant application, it is intended that all matters contained in the foregoing description or shown in the accompanying drawings shall be interpreted as illustrative and not in a limiting sense.

The disclosure is not intended to be limited to the particular forms disclosed. Rather, the disclosure is to cover all modifications, equivalents, and alternatives falling within the scope of the disclosure as defined by the following appended claims and their legal equivalents.

All publications, patents, and patent documents cited in this specification are incorporated herein by their reference, as though individually incorporated by reference.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

It is also to be understood that the following claims are intended to cover all of the generic and specific features of the invention herein described, and all statements of the scope of the invention that, as a matter of language, might be said to fall therebetween.

What is claimed is:

1. An infusion device configured to deliver a fluidic drug to a patient's tissue, the infusion device comprising:
    a fluid input line fluidically coupled to an infusion hub at an inlet port, wherein the infusion hub resides within a patient when implanted and the input line extends out of the patient to connect to a fluid reservoir;
    the infusion hub having a plurality of outlet ports;
    a first indwelling delivery tube attachable to the infusion hub, the first indwelling delivery tube having:
        an internal lumen, an inlet aperture leading to the internal lumen, and an exit aperture through which the fluidic drug can exit the internal lumen of the delivery tube, wherein the internal lumen is comprised of a predetermined material with a known elasticity;
        a length to bring the exit aperture into close proximity with a target tissue for delivering the fluidic drug to the target tissue;
    a second indwelling delivery tube attachable to the infusion hub, the second indwelling delivery tube having:
        an internal lumen, an inlet aperture leading to the internal lumen, and an exit aperture through which the fluidic drug can exit the internal lumen of the delivery tube, wherein the internal lumen is comprised of a predetermined material with a known elasticity;
        a length to bring the exit aperture into close proximity with a target tissue for delivering the fluidic drug to the target tissue; and
    the first and second indwelling delivery tubes having:
        at least a different length or a different lumen wall elasticity; and a same predetermined flow rate and a same impedance, wherein the flow rate and impedance for each of the first and second indwelling delivery tubes are based on the lengths, cross-sectional areas of the internal lumens, and the known elasticity of the internal lumens.

2. The infusion device of claim 1, further including delivery tube connectors between the infusion hub outlet ports and the first and second indwelling delivery tubes, wherein each delivery tube connector is adapted to pivot about at least one axis.

3. The infusion device of claim 1, further including channels extending between the inlet port and the outlet ports in the infusion hub.

4. The infusion device of claim 1, further including a pressurizer fluidically coupled to the infusion device.

5. The infusion device of claim 1, further including a fluid reservoir in fluidic communication with the fluid input line.

6. The infusion device of claim 1, wherein the first and second indwelling delivery tubes and the infusion hub reside entirely within a patient when implanted.

7. The infusion device of claim 1, further including delivery tips fluidically attached to or integrated with the first and second indwelling delivery tubes, wherein the delivery tips pierce the target tissue during insertion.

8. The infusion device of claim 1, wherein a radius of each of the internal lumens of the first and second indwelling delivery tube is calculated based on $$r = \sqrt[4]{\frac{8\mu LQ}{\Delta P \pi}},$$

where r is the radius of the internal lumen, Q is the flow rate of the fluidic drug, μ is a viscosity of the fluidic drug, L is the length of the internal lumen, and ΔP is the change in pressure of the fluid between the inlet and outlet of the delivery tube, and π is the mathematical constant pi.

9. The infusion device of claim 1, further including a third indwelling delivery tube attached or attachable to the infusion hub, the third indwelling delivery tube having:
an internal lumen, an inlet aperture leading to the internal lumen, and an exit aperture through which the fluidic drug can exit the internal lumen, wherein the internal lumen is comprised of a predetermined material with a known elasticity;
a known length and a known cross-sectional area; and
a predetermined flow rate and predetermined impedance, wherein the predetermined flow rate and predetermined impedance of the third indwelling tube are different than the predetermined flow rate and predetermined impedance of the first and second indwelling tubes.

10. A method of delivering a fluidic drug to a patient's tissue, comprising:
retrieving medical imaging of a treatment field within a patient;
identifying target tissue to be treated with the fluidic drug;
identifying an intended implantation location for an infusion hub, wherein the infusion hub is fluidically coupled to a fluid input line at an inlet port in the infusion hub and the infusion hub has a plurality of outlet ports;
determining a desired flow rate and a desired impedance of the fluidic drug through a plurality of delivery tubes fluidically coupled to the infusion hub via the outlet ports;
determining a length of each delivery tube to bring an exit aperture of the delivery tube into close proximity with the target tissue for delivering the fluidic drug to the target tissue;
based on the desired flow rate and the desired impedance of the fluidic drug through the plurality of delivery tubes and the length of each delivery tube, calculating a cross-sectional area of an internal lumen of each delivery tube such that each delivery tube has the same desired flow rate and the same desired impedance regardless of any differences in the lengths between each of the delivery tubes; and
implanting the infusion hub and the plurality of delivery tubes into the treatment field, thereby allowing the fluidic drug to be delivered to the patient's target tissue.

11. The method of claim 10, wherein the infusion hub further includes delivery tube connectors between the infusion hub outlet ports and each of the delivery tubes, wherein each delivery tube connector is adapted to pivot about at least one axis.

12. The method of claim 10, further including:
determining that certain target tissue in the treatment field requires a different flow rate of the fluidic drug than other target tissue in the treatment field;
attaching an alternative delivery tube to the infusion hub, wherein the alternative delivery tube includes:
an internal lumen, an inlet aperture leading to the internal lumen, and an exit aperture through which the fluidic drug can exit the internal lumen, wherein the internal lumen is comprised of a predetermined material with a known elasticity;
a known length and a known cross-sectional area; and
a predetermined flow rate and predetermined impedance, wherein the predetermined flow rate and predetermined impedance of the alternative delivery tube are different than the predetermined flow rate and predetermined impedance of the plurality of delivery tubes.

13. The method of claim 10, further securing a pressurizer to the infusion device.

14. The method of claim 10, further securing a fluid reservoir in fluidic communication with the fluid input line.

15. The method of claim 10, further including closing, in a fluid tight seal, outlet ports not connected to delivery tubes.

16. The method of claim 10, further including securing delivery tips to the delivery tubes, wherein the delivery tips are configured to pierce the target tissue during insertion.

17. The method of claim 10, wherein calculating the cross-sectional area of the internal lumens of each delivery tube includes calculating a radius of the internal lumens using the equation $$r = \sqrt[4]{\frac{8\mu LQ}{\Delta P \pi}},$$

where r is the radius of the internal lumen, Q is the flow rate of the fluidic drug, μ is a viscosity of the fluidic drug, L is the length of the internal lumen, and ΔP is the change in pressure of the fluid between the inlet and outlet of the delivery tube, and π is the mathematical constant pi.

18. An infusion delivery device kit, comprising:
a fluid input line fluidically coupled or attachable to an infusion hub at an inlet port;
the infusion hub having a plurality of outlet ports;

a first plurality of delivery tubes, each having a same predetermined first length and a same first internal cross-sectional area;
a second plurality of delivery tubes, each having a same predetermined second length and a same second internal cross-sectional area;
the first plurality of delivery tubes and second plurality of delivery tubes integrated with or configured to attach to the infusion hub to bring the delivery tubes in fluid communication with the outlet ports on the infusion hub;
the first length being distinct from the second length;
the first cross-sectional area being distinct from the second cross-sectional; and
the first plurality of delivery tubes and second plurality of delivery tubes having a same predetermined flow rate and a same impedance.

19. The infusion delivery device kit of claim 18, further including delivery tube connectors attachable to or pre-attached to the infusion hub and the delivery tubes, wherein each delivery tube connector is adapted to pivot about at least one axis.

20. The infusion delivery device kit of claim 18, wherein a radius of the internal cross-sectional areas of each of the first and second delivery tubes is calculated based on $$r = \sqrt[4]{\frac{8\mu LQ}{\Delta P \pi}},$$

where r is the radius of the radius of the internal cross-sectional area, Q is the flow rate of a fluidic drug, $\mu$ is a viscosity of the fluidic drug, L is the length of the delivery tubes, and $\Delta P$ is the change in pressure of the fluid drug between an inlet and an outlet of the delivery tubes, and $\pi$ is the mathematical constant pi.

* * * * *